United States Patent [19]

Martin, Jr. et al.

[11] Patent Number: 4,743,252
[45] Date of Patent: May 10, 1988

[54] COMPOSITE GRAFTS

[75] Inventors: John B. Martin, Jr.; David C. MacGregor; Leonard Pinchuk, all of Miami, Fla.

[73] Assignee: Corvita Corporation, Miami, Fla.

[21] Appl. No.: 818,483

[22] Filed: Jan. 13, 1986

[51] Int. Cl.$^4$ .............................................. A61F 2/06
[52] U.S. Cl. ......................................... 623/1; 623/11
[58] Field of Search ............................... 623/1, 66, 11; 128/334 R

[56] References Cited

U.S. PATENT DOCUMENTS

| | | |
|---|---|---|
| 2,411,660 | 11/1946 | Manning . |
| 2,886,877 | 5/1959 | Frickert et al. . |
| 4,044,404 | 8/1977 | Martin et al. . |
| 4,323,525 | 4/1982 | Bornat . |
| 4,475,972 | 10/1984 | Wong . |

FOREIGN PATENT DOCUMENTS

| | | | |
|---|---|---|---|
| 0117072 | 8/1984 | European Pat. Off. ................ | 623/1 |
| 0157178 | 10/1985 | European Pat. Off. ................ | 623/1 |
| 0190966 | 9/1985 | Japan .................................... | 623/1 |
| 2077107 | 12/1981 | United Kingdom .................... | 623/1 |

OTHER PUBLICATIONS

Article, Annis, et al, "An Elastomeric Vascular Prosthesis", Trans.Am.Soc.Artif.Intern.Organs, vol. XXIV, pp. 209–214, (1978).
Leidner et al, "A Novel Process for the Manufacturing of Porous Grafts: Process Description and Product Evaluation", Journal of Biomedical Materials Research, vol. 17, pp. 229–247, (1983).

Primary Examiner—Richard J. Apley
Assistant Examiner—Alan W. Cannon
Attorney, Agent, or Firm—Lockwood, Alex, Fitzgibbon & Cummings

[57] ABSTRACT

Composite grafts are provided that have a porous wall structure to permit ingrowth thereinto under in vivo conditions but which include a generally non-porous membrane in the wall to prevent substantial fluid passage therethrough so as to provide an implantable porous graft that does not require preclotting prior to implantation. One or more of such membranes are formed in place by applying a polymeric membrane-forming composition during the formation of a graft body by winding elongated extruded fibers on a mandrel.

9 Claims, 1 Drawing Sheet

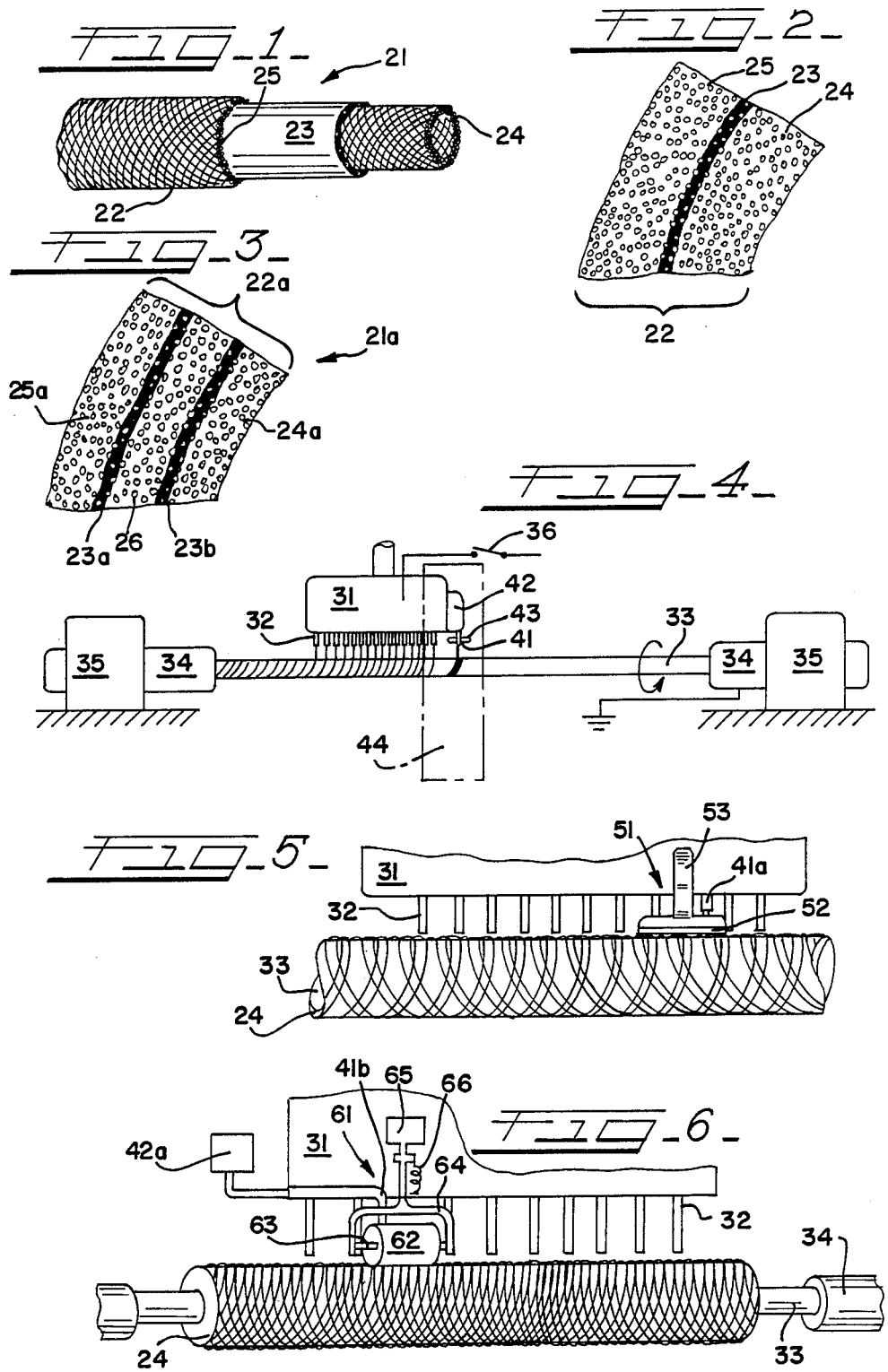

COMPOSITE GRAFTS

BACKGROUND AND DESCRIPTION OF THE INVENTION

The present invention generally relates to composite grafts that have a generally porous graft body and a generally non-porous membrane. The composite graft is of the non-braided and non-woven type, its body has a porosity that provides an environment which is conducive to tissue ingrowth thereinto, and the membrane of the composite graft is a substantially non-porous cylinder. The graft body is formed from a fiber-forming polymer which is extruded into fibers that are wound or spun onto a mandrel, while the membrane is a biocompatible elastomeric polymer sheath that is formed in place on the mandrel, typically being formed on a partially spun vascular graft body. Formation of the membrane is carried out by a procedure that includes directing a polymeric membrane-forming composition toward the mandrel. Typically, the remainder of the graft body will thereafter be wound over the formed membrane in order to provide a composite graft having a porous graft body with a substantially non-porous cylindrical membrane embedded therewithin to thereby provide a composite graft that is porous to promote ingrowth but that has essentially leak-proof sidewalls.

Graft products such as vascular grafts are known to be made by methods which include winding extruded material onto a mandrel in an attempt to provide a degree of porosity that is desired for implantable grafts, especially including providing an ingrowth environment that is particularly suitable for promoting tissue ingrowth at the implantation locations. One such approach is detailed in U.S. Pat. No. 4,475,972, the disclosure of which is incorporated by reference hereinto. That patent describes non-woven vascular grafts that are made by extruding a polyurethane solution under pressure through an opening and then drawing the extruded material while winding same on the mandrel.

While the porosity that is provided by these types of vascular graft structures is extremely desirable and advantageous, a porous vascular graft substrate or wall is, prior to implantation, typically also porous to the extent that blood or other fluids can pass through the porous wall or porous substrate. Typically, before such a porous implantable device is implanted, the surgical team must subject it to preclotting with blood or the like in order to prevent fluid loss upon initial pressurization of the vascular graft. Such a preclotting step is considered to be a time-consuming annoyance and can provide a potential opportunity for the development of thrombosis and/or infection. Also, the preclotting procedure can vary the environment provided by the vascular graft depending upon the manner in which the techniques are employed by the individuals carrying out the preclotting procedure, which can affect the reproducibility of vascular graft implantation techniques.

The problem of attempting to eliminate the need for preclotting of vascular grafts is rendered more difficult because, for many vascular grafts, it is important to provide certain porosity properties for both internal and external surfaces thereof. In the example of a tubular vascular graft, its external cylindrical surface can be rendered porous in order to provide a porous depth that affords a means for fixation to host tissues by soft tissue ingrowth into the porous depth of the surface, while the internal generally cylindrical porous surface affords a porous interface having smaller pore sizes which provide tissue-implant interfaces that are blood compatible arising from colonization and tissue formation on the blood-contacting internal surface of such vascular grafts. In such instances, tissue ingrowth is desired on the external surface, while endothelial-like cell ingrowth provided by nucleated blood cells or the like is desired on the internal surface. For these reasons, it may be most desirable to provide a vascular graft that is porous on both of its surfaces, but that still prevents fluid passage from one surface to the other without requiring a preclotting operation or the like.

These aspects which are associated with porous vascular grafts in general are taken into consideration by the present invention, which, in summary, includes a substantially non-porous membrane that is formed in place and in association with the spinning and winding procedure that is used to form the graft. More particularly, the present invention is a composite graft that includes a generally porous graft body which is formed by extruding a fiber-forming polymer in association with a rotating mandrel and that further includes a generally non-porous membrane that is formed in place within, under or over the body and also in association with the rotating mandrel. In one embodiment, this membrane formation includes an electrostatically assisted deposition of a biocompatible elastomeric polymer. In its preferred form, the composite graft is made by first partially forming the graft body, suitably depositing the elastomeric polymer and forming the membrane, and then completing the winding of the graft body. A preferred membrane-forming biocompatible elastomeric polymer is a silicone rubber material.

It is accordingly a general object of the present invention to provide an improved non-woven graft.

Another object of this invention is to provide an improved graft having a porous surface for promoting ingrowth and a non-porous membrane.

Another object of the present invention is to provide an improved graft and method for making same that has a porous ingrowth surface but does not permit the passage of fluids therethrough.

Another object of this invention is to provide an improved porous graft and method of making same which does not require preclotting.

These and other objects, features and advantages of this invention will be clearly understood through a consideration of the following detailed description.

BRIEF DESCRIPTION OF THE DRAWINGS

In the course of this description, reference will be made to the attached drawings, wherein:

FIG. 1 is a perspective view, partially cut away, of a composite graft according to this invention;

FIG. 2 is a transverse cross-section of a segment of the graft illustrated in FIG. 1;

FIG. 3 is a cross-section similar that of FIG. 2, but of a segment of a composite graft having a plurality of membranes;

FIG. 4 is a generally schematic view illustrating a step in the method of forming the composite graft and showing one embodiment of the mechanism for forming the membrane;

FIG. 5 is an enlarged view of a portion of an apparatus as generally illustrated in FIG 4 but which utilizes additional or alternative blade means for forming the membrane; and FIG. 6 is an enlarged view of a portion of an apparatus as generally illustrated in FIG. 4 but which utilizes additional or alternative roller means for forming the membrane.

DESCRIPTION OF THE PARTICULAR EMBODIMENTS

In the embodiment illustrated in FIGS. 1 and 2, a composite graft, generally designated as 21, includes a graft body 22 and a membrane 23. The graft body 22 includes an internal cylindrical portion 24 and an external cylindrical portion 25 which are separated from each other by the membrane 23. Membrane 23 is intimately secured to both cylindrical portions of the graft body 22, and the composite graft 21 is a unitary vascular graft.

FIG. 3 illustrates the composite graft 21a having a plurality of membranes 23a, 23b interposed within graft body 22a, which includes an internal cylindrical portion 24a, an external cylindrical portion 25a, and an intermediate cylindrical portion 26. Each of the plurality of membranes 23a, 23b is securely embedded between the respective cylindrical portions 24a, 25a and 26 in order to provide a composite graft 21a which, as is the case for composite graft 21, is a securely assembled composite product that functions as a unitary graft which does not require preclotting.

Regarding the apparatus illustrated in FIG. 4, which is suitable for carrying out the process according to the present invention, such includes a distributor 31 for achieving formation of polymeric from fine orifices 32, typically in conjunction with formation of those fibers from a fiber-forming polymeric solution by generally known extrusion techniques. Before such fibers are fully set, they are wound onto a mandrel 33, which is typically rotated within suitable jaws 34. In the arrangement illustrated, the distributor 31 moves back and forth within a plane generally between the jaws 34, while the mandrel 33 is rotated by suitable means such as the illustrated motors 35. Alternatively, the distributor 31 can take the form of a spinnerette that rotates around the mandrel 33. Whatever mechanism or technique is utilized, such will result in combined rotational and translational relative movement between the polymeric fibers 32 and the mandrel 33. A desired number of layers of polymeric fibers are laid down over the mandrel 33. Although the membrane(s) of the composite graft according to this invention can be positioned at any desired location, typically such will be formed during an interruption in this operation by which the polymeric fibers are laid down to form the respective cylindrical portions of the composite graft.

The illustrated apparatus can include electrostatic charge generation components in order to develop an electrostatic charge between the distributor 31 and the mandrel 33. Preferably, the mandrel 33 is grounded or negatively charged, while the distributor 31 is positively charged when a switch 36 or the like is closed. Alternatively, the distributor can be grounded and the mandrel can be positively charged. These electrostatic charge components can be used in connection with formation of the graft body, as well as formation of the membrane(s).

When the electrostatic charge generation components are used in conjunction with the formation of the graft body, which is specified in greater detail in a copending application entitled "Implantable Vascular Grafts" and filed Nov. 21, 1985, the polymeric fibers accelerate, upon application of the electrostatic charge, from the distributor 31 to the mandrel 33 to a speed that is faster than that which is achieved during spinning and drawing in the absence of the electrostatic field. Distributor 31 may include any number of individual extrusion orifices or hypodermic cylinders 32 as illustrated. Imparting the electrostatic field for this purpose remedies breakage of the forming polymeric fibers; acceleration of a broken strand away from the hypodermic cylinder 32 is achieved so that the free end thereof substantially contacts and adheres to the forming graft. This formation is facilitated by virtue of the fact that the rapid acceleration caused by the electrostatic force directs the fiber to the mandrel and enhances the ability of the broken end to reach the forming graft cylinder before the polymeric fibers have set, which is typically while the extruded polymeric material still includes enough unevaporated solvent so as to maintain same in a condition that promotes fiber adhesion. Without application of the electrostatic field in this regard, the free end dangling from the distributor 31 will pendulum into the other fibers causing additional fiber breakage.

This type of development of the electrostatic field between the hypodermic cylinders 32 and the mandrel 33 can also, as described in said copending application, be used to provide the graft with sections of reduced porosity, which is often desired for the internal surface of the graft. Additionally, this mode of applying the electrostatic field can be used during winding of the last few (for example about 3) passes on the outer surface of the graft in order to prevent the outer surface from becoming scraggly when it is handled.

This same general type of electrostatic field generation can be used in conjunction with carrying out the present invention by developing the electrostatic charge between the mandrel 33 and a selected nozzle 41 (FIG. 4) that is provided for discharging a polymeric composition in order to form the membrane(s) of the composite graft. Nozzle 41 is in communication with a suitable reservoir 42 which may move with the distributor 31 or be positioned at a remote location as desired (not shown). The reservoir may be pressurized to force viscous membrane-forming material through the nozzle 41. Nozzle 41 typically has associated therewith a flow controlling assembly 43 that can take the form of the illustrated stopcock or any other valve including remote activating valves such as solenoid valves, the opening of which permits passage of the polymeric membrane-forming composition through the nozzle 41 and onto the mandrel 33 or onto the partially formed composite graft wound thereon.

The nozzle can be configured as a cylindrical or tubular spinnerette, or it can be configured as a rectangular or slotted spinnerette. Fibers are formed when polymer is extruded through the tubular nozzle, ribbons are formed when polymer is extruded through a slotted nozzle. Henceforth the term "nozzle" refers to both cylindrical (tubular) and rectangular (slotted) orifices.

Flow control can also be implemented or supplemented by adjusting the pressure in the reservoir for the membrane-forming material. Application of the electrostatic field in this embodiment facilitates rapid and substantially complete passage of the polymeric membrane-forming composition through the nozzle 41 and onto the mandrel or partially formed vascular graft body. It also minimizes the possibility that the polymeric composition will splatter. However, deposition of the membrane-forming composition can be achieved directly without implementation of the electrostatic field.

The illustrated polymeric composition dispensing assembly for forming the membrane can include a temperature assembly 44 that can be useful in altering the temperature, typically raising it, so as to vary the temperature at the dispensing assembly and, preferably, also around the mandrel 33. The uncured, highly viscous polymeric membrane-forming material can be deposited without dilution directly toward the rotating mandrel by forcing the polymeric material through the nozzle 41 by pressurizing reservoir 42 with compressed air or nitrogen gas. However, typically, the membrane-forming composition will include a solvent that has a relatively low boiling point such that when the polymeric membrane-forming composition is at a predetermined temperature, such as through the use of the temperature control assembly 44, the solvent will be raised above its boiling point, thereby causing it to boil and raise the pressure in the reservoir 42. With the flow control assembly 43 open, the thus pressurized solvent (together with the membrane-forming polymer that is dissolved or dispersed therein) is thus forced through the nozzle 41 and toward the mandrel 33. When the electrostatic field is applied between the nozzle 41 and the mandrel 33, such facilitates precise and rapid direction of the membrane-forming polymer to its desired location in order to form the membrane. Because the solvent is above its boiling point, it will flash off almost immediately in order to leave a thin coating of the membrane-forming polymer on the mandrel or graft in order to thereby form the membrane in place or in situ with respect to the graft. Such immediate flashing reduces the chance that polymeric solution will block pores on the inner surface of the graft or will wick down into the pores and thereby form pores in the membrane, rather than providing an impermeable or non-porous membrane.

FIG. 5 illustrates an alternative assembly for spreading the polymeric membrane composition onto the mandrel or partially formed graft, such including a doctor blade assembly, generally designated as 51, for spreading the polymeric membrane composition in a thin layer from nozzle 41a. The doctor blade assembly 51 reduces the importance of providing the electrostatic field at the nozzle 41a and of the development of an elevated pressure in the polymeric membrane-forming composition dispensing assembly. This is due in large measure to the fact that the doctor blade assembly 51 will physically contact the polymeric membrane-forming composition and direct same onto the mandrel or partially formed graft. However, the doctor blade assembly 51 can be used in conjunction with the electrostatic field and a pressurized reservoir if so desired.

Doctor blade assembly 51 includes a doctor blade 52 and a mounting arm 53 for conveniently affixing the doctor blade 52 to the distributor 31. A typical spacing between the working edge of the doctor blade 52 and the mandrel or graft is between about 1 micron and about 60 microns in order to form a membrane having a thickness generally in accordance with this invention, which is between about 1 and 100 microns, more typically between about 5 and 40 microns. If desired, the membrane may be formed in a single pass through a slotted nozzle, although typically multiple passes will be practiced for this embodiment, although other embodiments of this invention typically require a greater number of multiple passes.

The embodiment illustrated in FIG. 6 includes a roller assembly, generally designated as 61, somewhat analogous to the doctor blade assembly 51, except the surface that engages the mandrel or the partially formed graft is a freely rotating roller 62 that is biased into engagement with the mandrel or partially formed graft. More particularly, roller 62 is rotatably mounted onto an axle 63 mounted onto a yoke 64 and hinged arm 65 that is secured to the distributor 31. Preferably a spring 66 or other suitable biasing means applies a slight force in order to lightly urge the roller 62 into engagement with the mandrel or graft and to dampen bouncing of the roller due to vibration of the mandrel. Nozzle 41b directs polymeric membrane-forming composition from a dispensing assembly 42a, either with or without the aid of the electrostatic field. The polymeric membrane-forming composition is dispensed onto the roller 62 or directly onto the mandrel or graft and is rolled into the graft, with the roller imparting enhanced and deeper penetration of the polymeric membrane composition into interstices of the graft. biasing spring can be adjusted to vary the depth of penetration of the membrane material into the graft interstices. The thickness of the graft can be controlled by limiting the number of coatings of the membrane material or by varying the orifice diameter or slot thickness or by varying the rate of flow of polymer through the orifice.

In connection with any of the illustrated embodiments, dispensing of the polymeric membrane-forming composition from the dispensing assembly can be facilitated by imparting energy thereto, particularly to the nozzle 41, 41a, 41b. Similarly, the membrane-forming composition can be used without dilution or it can be thinned with appropriate solvents to facilitate dispension and penetration into the graft interstices. Such procedures and assemblies can also result in the formation of an atomized type of dispensing from the nozzle toward the mandrel, which can result in the formation of an atomization discharge toward the mandrel, including a charged beam of polymeric composition. Devices or assemblies that provide atomization in this regard include electrostatic generating devices, ultrasonic transducers or resonators, piezoelectric crystals or transducers, buzzer relays, oscillating magnetic fields, oscillating inductor coils and oscillating electric fields. The resulting atomized stream minimizes the formation of globules or uneven surfaces of the membrane.

The polymeric material from which the graft fibers are extruded must be a fiber-forming type of polymer; that is, the polymer must be capable of being formed as a fiber when extruded through a fine orifice and into the air. For example, polyamides such as the nylons and regenerated cellulose products such as the rayons are fiber forming. However, many currently available fiber forming polymers are unsuitable for implantation uses or do not possess the properties needed for a flexible graft, such as reasonable pliability, elasticity and biocompatibility. Such polymeric materials also should form a viscous solution in volatile solvents from which continuous fibers may be withdrawn. As a general class of polymers, the polyurethanes tend to possess the physical properties that are desirable for the manufacture of grafts such as grafts. However, segmented polyurethanes as a class are typically not looked upon as being fiber-forming in air, and when extruded they tend to exhibit excessive breakage. Nevertheless, polyurethanes of the type that are fiber-forming are generally preferred.

Such fibers, when set, form a generally cylindrical elongated graft which has an inside diameter that is substantially the same as the outside diameter of the mandrel 33. Individual fibers are bound to each other, generally at most if not substantially all of the locations where the fibers intersect or otherwise contact each other. This fiber-to-fiber bonding results when the solvent-containing and only partially set fibers engage one another during winding, which is typically facilitated by drawing the extruded fibers over fibers lying thereunder, such being suitably accomplished by selecting an appropriate speed of relative movement between the mandrel 33 and the distributor 31 which will draw the fibers at a speed that is faster than the rate by which they are extruded from the distributor 31.

The polymeric membrane-forming composition includes membrane-forming polymeric material that is biocompatible and preferably elastomeric, that is substantially soluble in a selected solvent that will not damage the graft fibers and that is readily curable so as to rapidly form the membrane in place. Exemplary polymers include silicone rubber type materials, natural latex rubber, ethylene vinyl acetate, styrene-butadiene homopolymers, blends or copolymers, including styrene-butadiene block copolymers, styrene-isoprene homopolymers, blends or copolymers, including styrene-isoprene block copolymers, as well as polyethylenes, polyesters, and fluoroelastomers such as copolymers of vinylidene fluoride and hexafluoropropylene.

With more particular reference to silicone rubber types of materials, such are preferably siloxanes having

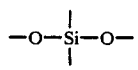

groups. A representative siloxane component, prior to curing, can be represented by the formula:

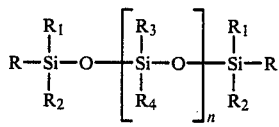

wherein each of R, $R_1$ and/or $R_2$ can be a group such as an ester moiety, an acetoxy moiety, an alcohol moiety and the like that are involved in the crosslinking, curing or polymerizing of the siloxane component. $R_3$ and $R_4$, as well as $R_1$ and $R_2$, can each be aliphatic or aromatic groups such as methyl, ethyl, propyl, phenyl, or substituted aliphatics or aromatics containig halogen moieties or other groups, for example 3,3,3-trifluoropropylmethyl moieties. This general formula represents a siloxane component that can react with itself with or without the presence of moisture and/or a catalyst in order to crosslink or polymerize into the silicone elastomer. If at least the R groups are alcohol moieties, the silicone elastomer can be formed by reaction with a suitable crosslinking component.

An exemplary silicone elastomer or rubber is a siloxane condensation reaction product, the principal reactants of which include a silicone moiety:

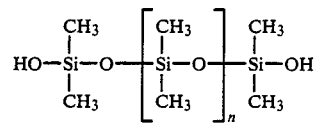

wherein n has an average value of greater than 100. Another principal reactant is an acetoxy silane crosslinker of the formula:

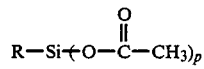

wherein p is 1,2 or 3. The exemplary siloxane of this type is poly(dimethyl siloxane). Other siloxane polymers include poly(ethylmethyl siloxane), poly(3,3,3-trifluoropropylmethyl siloxane) and copolymers of these types of siloxanes with poly(dimethyl siloxane). Polymeric siloxanes are generally known and are available commercially, for example, from Dow Corning Corporation. Siloxanes are generally described in U.S. Pat. No. 3,434,869, the subject matter of which is incorporated by reference hereinto.

The polymeric membrane-forming composition in accordance with this invention may or may not include a solvent for dissolving the elastomeric polymer material. If a solvent is used, such should be a solvent that will not cause dissolution of or otherwise detrimentally affect the underlying graft fibers. It is typically advantageous that such solvent have a relatively low boiling point. The polyhalogenated hydrocarbons and the like are especially preferred. Exemplary polyhalogenated hydrocarbons include materials available under the Freon trademark, including trichlorofluoromethane, dichlorodifluoromethane, 1,2-dichloro-1,1,2,2-tetrafluoroethane and octafluorocyclobutane. Certain of these polyhalogenated hydrocarbons exhibit atmospheric boiling points below room temperature, and these solvents can be advantageously used as components of the polymeric membrane-forming composition by maintaining the composition at an appropriate elevated pressure and/or decreased temperature under conditions such that the solvent readily evaporates (when no longer exposed to such conditions) to achieve the desired flash removal of the solvent from the surface of the membrane as it is forming on the mandrel or graft. Exemplary appropriate conditions in this regard could be those generally understood to exist in connection with so-called aerosol containers.

Typically, the polymeric membrane-forming composition includes between about 1 to 60 percent, preferably between 35 and 45 percent, of the elastomeric polymeric material, with the balance being primarily the selected solvent system. The quantity of the solvent and the volatility of the solvent can be generally less when the applying mechanism used is on the order of the illustrated doctor blade assembly or roller assembly, since both achieve a smoothing of the elastomeric polymer component and a dispersing of same substantially evenly along the length of the graft. The elastomeric polymer material preferably penetrates into the porous graft from about 2 to about 10 windings or fiber layers in depth. Extensive penetration into the graft can cause unwanted stiffening of the graft.

Selection of the location of the membrane(s) substantially anywhere along the wall thickness of the graft is possible. Usually, placement is desired at a location within the graft so as to provide exposed porous surfaces for the graft, although placement can be made at the innermost surface or at the outermost surface. Typically, the spinning process used to form the graft will be stopped at a predetermined graft thickness, and the membrane will be applied as described herein. Often, preferred placement is from one quarter to three quarters of the distance from the internal surface or lumen to the designed exterior surface of the graft. After each desired membrane is applied, graft spinning resumes until the remainder of the graft is spun.

The formed grafts may vary in dimensions as desired. The inside diameter will depend upon the size of the mandrel, a typical range for vascular grafts being as fine as a diameter of 0.001 inch, with a practical upper limit being on the order of 2 inches or more, the larger sized grafts being suitable, for example, to be cut into flat sheets or otherwise shaped for making gauze types of products, shunts, bladders, ureters, urethras, sewing rings and patches, diaphragms and the like for various types of reconstructive surgical procedures. More usual inside diameters range between about 1 mm to about 50 mm. Graft wall thicknesses are determined by the number of layers of windings and the thicknesses of the individual wound fibers or ribbons, as well as the wetness of the fibers when applied onto each other and, when utilized, the electrostatic field which causes applied polymer to sink into underlying fibers.

When the term non-porous graft is used herein, it is understood to include the types of products mentioned herein which have a membrane that is generally non-porous. Such generally non-porous nature includes a situation in which there is virtually no fluid leakage across the membrane, as well as a situation in which the membrane has one or more very fine holes or pin holes which permit "sweating" of the graft material or very minimal passage of fluids therethrough after implantation. Such a condition can manifest itself when the membrane is relatively thin, on the order of 50 microns or less. In certain instances, such sweating is believed to be beneficial because it permits fluid exchanges across the membrane for nourishment and waste disposal between cells.

Typically, the electrostatic field which can be generated and optionally utilized in accordance with this invention in connection with the formation of the graft body will be between about 1 and about 40 Kilovolts, preferably at about 20 Kilovolts (microamp current). The electrostatic field that can be generated in conjunction with application of the polymeric membrane-forming composition will be between about 1 and about 20 Kilovolts.

It will be understood that the embodiments of the present invention which have been described are illustrative of some of the applications of the principles of the present invention. Numerous modifications may be made by those skilled in the art without departing from the true spirit and scope of the invention.

We claim:

1. A porous biocompatible composite graft that is resistant to the passage of fluids through its walls, comprising:

a plurality of layers of biocompatible polymeric fiber material, said fiber layers having been formed by extrusion of a fiber-forming polymer through an orifice to form an elongated fiber that was wound on a mandrel to form a plurality of windings defining said plurality of layers, said plurality of windings defining a non-woven generally porous graft body having overlying fibers that intersect one another to form at least one porous wall of a predetermined thickness that is conducive to tissue ingrowth thereinto;

a generally cylindrical generally non-absorbable non-porous membrane sheath formed in place with respect to the mandrel and at least one of said plurality of layers of the generally porous graft body;

said generally cylindrical generally non-absorbable non-porous membrane sheath was formed in place from a polymeric membrane-forming composition; and said generally non-absorbable, non-porous membrane sheath is generally interposed between generally consecutive ones of said layers of the generally porous graft body in order to thereby define an internal cylindrical portion of the generally porous graft body and an external cylindrical portion of the generally porous graft body.

2. The composite graft according to claim 1, including a plurality of said generally cylindrical generally non-porous membrane sheaths, each of which is generally interposed between respective generally consecutive ones of said layers of the vascular graft generally porous body in order to thereby define an internal cylindrical portion, an intermediate cylindrical portion and an external cylindrical portion of the vascular graft generally porous body.

3. The composite graft according to claim 1, wherein said intermittent electrostatic field was applied during formation of at least the innermost one of said plurality of windings in order to provide an inner surface having a porosity less than that of a porous outer surface of the graft generally porous body.

4. The composite graft according to claim 1, wherein said graft generally porous body is spun from a fiber-forming polyurethane material, and wherein said membrane sheath is a silicone rubber material.

5. The composite graft according to claim 1, wherein said generally non-absorbable non-porous membrane sheath is located at substantially the innermost extent of the composite graft.

6. The composite graft according to claim 1, wherein said generally non-absorbable non-porous membrane sheath is located at substantially the outermost extent of the composite graft.

7. The composite graft according to claim 1, wherein the composite graft is cut in a generally longitudinal manner.

8. The composite graft according to claim 1, wherein the composite vascular graft is a product selected from the group consisting of a vascular grafts a gauze product, a shunt, a bladder, a ureter, a urethra, a sewing ring, a patch, a diaphragm, and the like.

9. The composite graft according to claim 1, wherein said generally non-absorbable non-porous membrane sheath includes very fine holes that permit fluid sweating therethrough.

* * * * *

UNITED STATES PATENT AND TRADEMARK OFFICE
CERTIFICATE OF CORRECTION

PATENT NO. : 4,743,252

DATED : May 10, 1988

INVENTOR(S) : Martin, Jr. et al.

It is certified that error appears in the above-identified patent and that said Letters Patent are hereby corrected as shown below:

Title page:

Under References Cited, U.S. PATENT DOCUMENTS, after line 2, insert
--3,914,802   10/1975   Reick.....623/1--
Under FOREIGN PATENT DOCUMENTS, after line 4, insert
--2,541,838   9/1984   France....623/1
  2,929,246   2/1980   West Germany....623/1--.
  Col. 2, line 58, after "similar", add --to--.
  Col. 6, line 21, before "biasing", insert --The--; line 63, after "such as", add --vascular--.
  Col. 10, lines 31-32, "vascular graft generally porous" should read --generally porous graft--; lines 34-35, "vascular graft generally porous" should read --generally porous graft--; line 41, "graft generally porous" should read --generally porous graft--; line 43, "graft generally porous" should read --generally porous graft--; line 58, delete "vascular"; line 59, "grafts" should read --graft,--.

Signed and Sealed this

Tenth Day of January, 1989

*Attest:*

DONALD J. QUIGG

*Attesting Officer*  *Commissioner of Patents and Trademarks*